US006026809A

United States Patent [19]

Abrams et al.

[11] Patent Number: 6,026,809

[45] **Date of Patent: *Feb. 22, 2000**

[54] INHALATION DEVICE

[75] Inventors: Andrew L. Abrams, Westport, Conn.; Anand V. Gumaste, Robbinsville, N.J.

[73] Assignee: Microdose Technologies, Inc., Monmouth Jct., N.J.

[ * ] Notice: Under 35 U.S.C. 154(b), the term of this patent shall be extended for 215 days.

[21] Appl. No.: 08/599,508

[22] Filed: Jan. 25, 1996

[51] Int. Cl.[7] .................................................... A61M 16/00

[52] U.S. Cl. ............................... 128/203.15; 128/203.12; 128/203.21; 128/200.22

[58] Field of Search ......................... 128/200.16, 203.12, 128/200.22, 200.23, 203.15, 203.21, 203.23, 204.21, 204.22; 604/58

[56] References Cited

U.S. PATENT DOCUMENTS

| | | | |
|---|---|---|---|
| 3,948,264 | 4/1976 | Wilke et al. | 128/266 |
| 3,957,965 | 5/1976 | Hartley et al. | 424/14 |
| 4,334,531 | 6/1982 | Reichl et al. | 128/200.14 |
| 5,284,133 | 2/1994 | Burns et al. | 128/203.15 |
| 5,312,281 | 5/1994 | Takahashi et al. | 446/25 |
| 5,349,947 | 9/1994 | Newhouse et al. | 128/203.21 |
| 5,372,128 | 12/1994 | Haber et al. | 128/203.21 |
| 5,452,711 | 9/1995 | Gault | 128/200.14 |
| 5,469,843 | 11/1995 | Hodson | 128/203.15 |
| 5,522,383 | 6/1996 | Calvert et al. | 128/203.15 |

FOREIGN PATENT DOCUMENTS

| | | | |
|---|---|---|---|
| 0174033 | 3/1986 | European Pat. Off. | 128/200.16 |
| 2072536 | 7/1981 | United Kingdom | B05B 3/02 |
| 2262452 | 6/1993 | United Kingdom | 128/203.15 |
| 9013327 | 11/1990 | WIPO | A61M 15/00 |
| 9013328 | 11/1990 | WIPO . | |

*Primary Examiner*—John G. Weiss
*Assistant Examiner*—V. Srivastava
*Attorney, Agent, or Firm*—Hayes, Soloway, Hennessey, Grossman & Hage, PC

[57] ABSTRACT

An inhaler that utilizes vibration to facilitate suspension of powder into a gas is provided. One embodiment of the inhaler includes a piezoelectric vibrator for vibrating the powder. A controller is provided for controlling supply of actuating electricity to the vibrator so as to cause the powder to vibrate in such a way as to optimally suspend at least a portion of the powder into the gas. The controller may include a user-actuable control for permitting the user to select the vibration frequencies and/or amplitudes for optimally suspending in the gas the type of powder currently being used in the inhaler.

29 Claims, 7 Drawing Sheets

INHALATION DEVICE

BACKGROUND OF THE INVENTION

1. Field of the Invention

The present invention relates generally to the field of inhalation devices, and more specifically, to inhalation devices that utilize vibration to facilitate suspension of powder (e.g., powdered medication) into an inhaled gas stream (e.g., of inhaled air). Particular utility for the present invention is found in the area of facilitating inhalation of powdered medications (e.g., bacterial vaccines, sinusitis vaccines, antihistaminic agents, vasoconstricting agents, anti-bacterial agents, anti-asthmatic agents, theophylline, aminophylline, di-sodium cromolyn, etc.), although other utilities are contemplated, including other medicament applications.

2. Brief Description of Related Prior Art

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the respiratory tract, it may be very rapidly absorbed into the blood stream; hence, this method of application may take the place of administration by injection, tablet, or other conventional means.

Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, issued to Hall, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the dispensing the powder into the stream of inhaled air. See also U.S. Pat. No. 5,458,135.

These prior art devices present several problems and posesses several disadvantages which are remedied by the inhalation devices of the present invention. For instance, these prior art devices require that the user exert extreme effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medicament. Another most important problem which has not been solved by the prior art devices is the presence of uncontrolled amounts or clumps of powdered material being inhaled into the user's mouth, rather than a constant inhalation of controlled amounts of finely dispersed powder.

The above description of the prior art is taken largely from U.S. Pat. No. 3,948,264 to Wilke et al, who disclose a device for facilitating inhalation of a powdered medication that includes a body portion having primary and secondary air inlet channels and an outlet channel. The secondary inlet channel provides an enclosure for a capsule containing the powdered medication and the outlet channel is formed as a mouthpiece protruding from the body. A capsule piercing structure is provided, which upon rotation puts one or more holes in the capsule so that upon vibration of the capsule by an electromechanical vibrator, the powdered drug may be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule. The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. According to Wilke et al, upon inhalation through outlet channel 3 and concurrent pressing of switch 10d to activate the electromechanical vibrating means 10, air is sucked through inlet channels 4 and 12 and the air stream through the secondary inlet channel 4 raises the capsule up against the vibrating plunger rod 10a. The capsule is thus vibrated rapidly with powder being fluidized and dispensed from the pierced holes therein. The air stream through inlet channel 4 and 12 aids in withdrawal of powder from the capsule and carries this powder through the outlet channel 3 to the mouth of the user." (Wilke et al, column 3, lines 45–55). Wilke et al further discloses that the electromechanical vibrator means may be placed at a right angle to the inlet chamber and that the amplitude and frequency of vibration may be altered to regulate dispensing characteristics of the inhaler.

Thus, as noted above, the vibrator in Wilke et al.'s disclosed inhaler is an electromechanical device consisting of a rod driven by a solenoid buzzer. A disadvantage of electromechanical vibrators of the type disclosed in Wilke et al. is that they include a relatively large number of mechanical moving parts that can be subject to significant wear and tear. Thus, disadvantageously, the inhaler disclosed in Wilke et al. requires frequent maintenance (e.g., to replace the mechanical moving parts that are subject to wear and tear).

Further disadvantageously, although Wilke et al. discloses that the amplitude and frequency of vibration may be varied in Wilke et al.'s disclosed inhaler in order to regulate dispensing characteristics of the inhaler, no means is provided in Wilke et al.'s disclosed inhaler to permit optimal adjustment of such vibration characteristics without disassembly of the inhaler and modification of the vibrator so as to vibrate at a different frequency and/or amplitude. Additionally, Wilke et al. nowhere discloses which amplitudes and frequencies of vibration are optimal for dispensing various types of powdered medications.

Moreover, as noted above, in Wilke et al.'s disclosed device, vibration of the powder is activated by depressing a push button. This can be difficult and painful for some users (e.g., patients suffering from extreme arthritis).

Finally, in order to use Wilke et al.'s disclosed inhaler most efficaciously, the user must depress the vibration-actuating push button at precisely the same time that the user begins inhalation. This can also be difficult for some users (e.g., very young patients, patients suffering from neuro-muscular disorders, etc.).

SUMMARY OF THE INVENTION

Thus, it is the general object of the present invention to provide an inhaler that utilizes vibration to facilitate suspension of powder into a gas that overcomes the aforesaid and other disadvantages and drawbacks of the prior art. Accordingly, one embodiment of the inhaler of the present invention includes a piezoelectric vibrator for vibrating the powder. A controller is provided for controlling supply (i.e., amplitude and/or frequency) of actuating electricity to the vibrator so as to cause vibration of the powder that is adapted to optimally suspend at least a portion of the powder into the gas. In this embodiment of the present invention, the controller may include a user-actuable control for permitting the user to select the vibration frequencies and/or amplitudes for optimally suspending in the gas the type of powder currently being used in the inhaler. The user-actuable control is pre-calibrated with the controller to cause the controller to adjust the frequency and/or amplitude of actuating electricity supplied to the vibrator to be that necessary for vibrating the type of powder selected by the user-actuable control in such a way as to optimally suspend at least a portion of the powder into the gas. The user-actuable control may include selection gradations in terms of the average size of the powder particles to be suspended in the gas, and/or in terms of desired vibration frequencies and amplitudes. Typically, for commonly used powdered medications of 0.5 to 10 micron size, more typically 1 to 5 micron size, vibration frequency would be adjusted to at least about 12 KHz, in order to optimally suspend such commonly used powdered medications in the gas. Of course, vibration frequency and amplitude may be adjusted to optimize suspension of the powdered medication being used.

Advantageously, the piezoelectric vibrator in this embodiment of the invention does not include the many moving mechanical parts of prior art electromechanical vibrator in the inhalers such as disclosed in Wilke et al. Thus, the vibrator in this embodiment does not require the frequent maintenance required by vibrator devices such as disclosed in Wilke et al. Further advantageously, the controller and user-actuable control of this embodiment of the present invention permit the vibration amplitude and frequency imparted to the powder to be quickly and easily adjusted for optimal delivery of different types of powders to the user without the inconvenience of having to disassemble and alter the physical components of this embodiment.

A second embodiment of the invention includes a controllable vibrator for vibrating the powder and a controller for controlling the vibrator. The controller controls the vibrator based, at least partially, upon at least one detected characteristic of the user's inhalation gas stream in and through the inhaler. The detected characteristics of the gas stream upon which the controller bases its control of the vibrator may include the detected velocity, flowrate, and/or pressure of the inhalation gas stream. The vibrator in this second embodiment may comprise a piezoelectric vibrator. Additionally, the controller of this second embodiment may control the vibrator by automatically actuating the vibrator when the at least one detected characteristic of the gas stream has a magnitude that exceeds a minimum threshold value therefor indicative of inhalation by the user, and by automatically deactivating the vibrator when the magnitude of the at least one detected characteristic is less then the minimum threshold.

This second embodiment may also include a plurality of gas inlets and at least one one-way valve in at least one of the inlets. The valve is adapted to permit flow of gas into the inhaler therethrough upon inhalation of gas from the inhaler.

This second embodiment may also include a dispenser for dispensing the powder for being vibrated. The dispenser dispenses the powder based upon control signals supplied to the dispenser by the controller. The controller generates these control signals based upon, at least in part, the at least one detected characteristic of the gas stream. The dispenser may dispense the powder directly to the surface of the vibrator.

Advantageously, these features of this second embodiment permit this embodiment to be able to commence dispensing and vibration of the powder simultaneously with inhalation by the user. Additionally, the one-way valve of this second embodiment prevents outflow of powder from the inhaler unless except during inhalation by the user. These features permit the powdered medication to be delivered to the user with much less waste and with a greater degree of dosage control than is possible according to the prior art.

In a third embodiment of the invention, a vibrator is provided for vibrating the powder. A controller is provided for controlling supply (i.e., frequency and/or amplitude) of actuating electricity to the vibrator based, at least in part, upon detected power transfer characteristics of the vibrator. Preferably, in this third embodiment, the detected power transfer characteristics upon which the controller bases its control of the supply of power include whether the maximum power is being transferred to the vibrator. The controller automatically adjusts the supply of power to the vibrator so as to maximize the detected power transferred to the vibrator.

Advantageously, it has been found that the powder is optimally suspended in the gas when detected power transferred to the vibrator is maximized. Thus, by utilizing the aforesaid automatic feedback and control features of this third embodiment of the present invention, the powder may be optimally suspended in the gas with little to no user interaction with the inhaler (i.e., the user does not need to adjust the frequency and/or amplitude of vibration himself).

These and other features and advantages of the present invention will become apparent as the following Detailed Description proceeds and upon reference to the Drawings, wherein like numerals depict like parts, and in which:

DETAILED DESCRIPTION OF PREFERRED EMBODIMENTS

Figure 2:
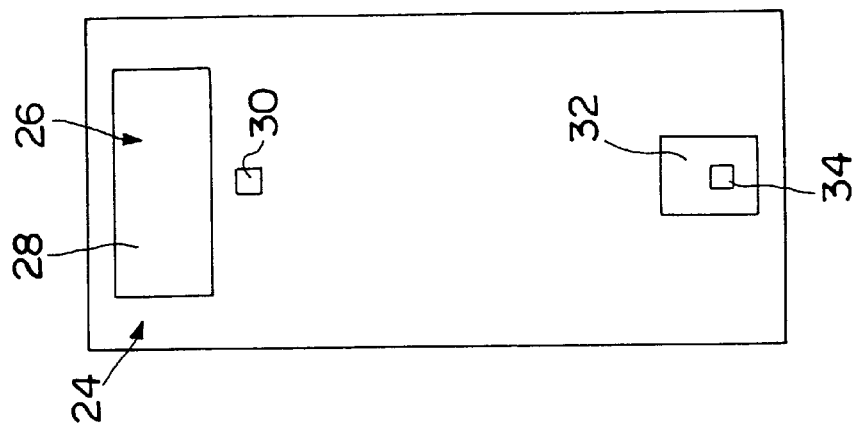
FIG. 2 is a rear plane view of the inhaler shown in FIG. 1.
Figure 1:
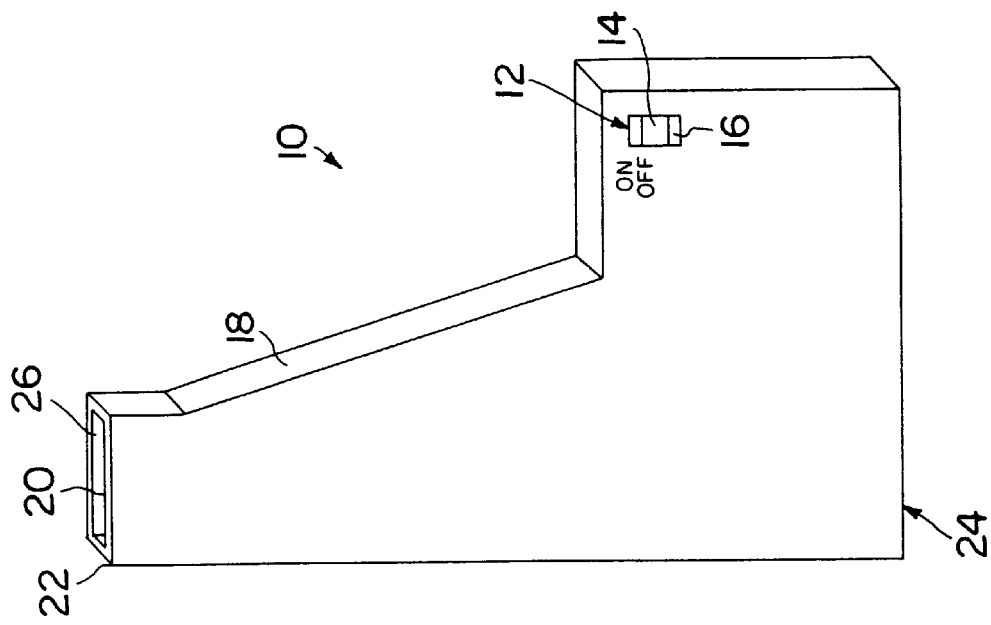
FIG. 1 is a perspective view of one embodiment of the inhaler of the present invention.
Figure 3:
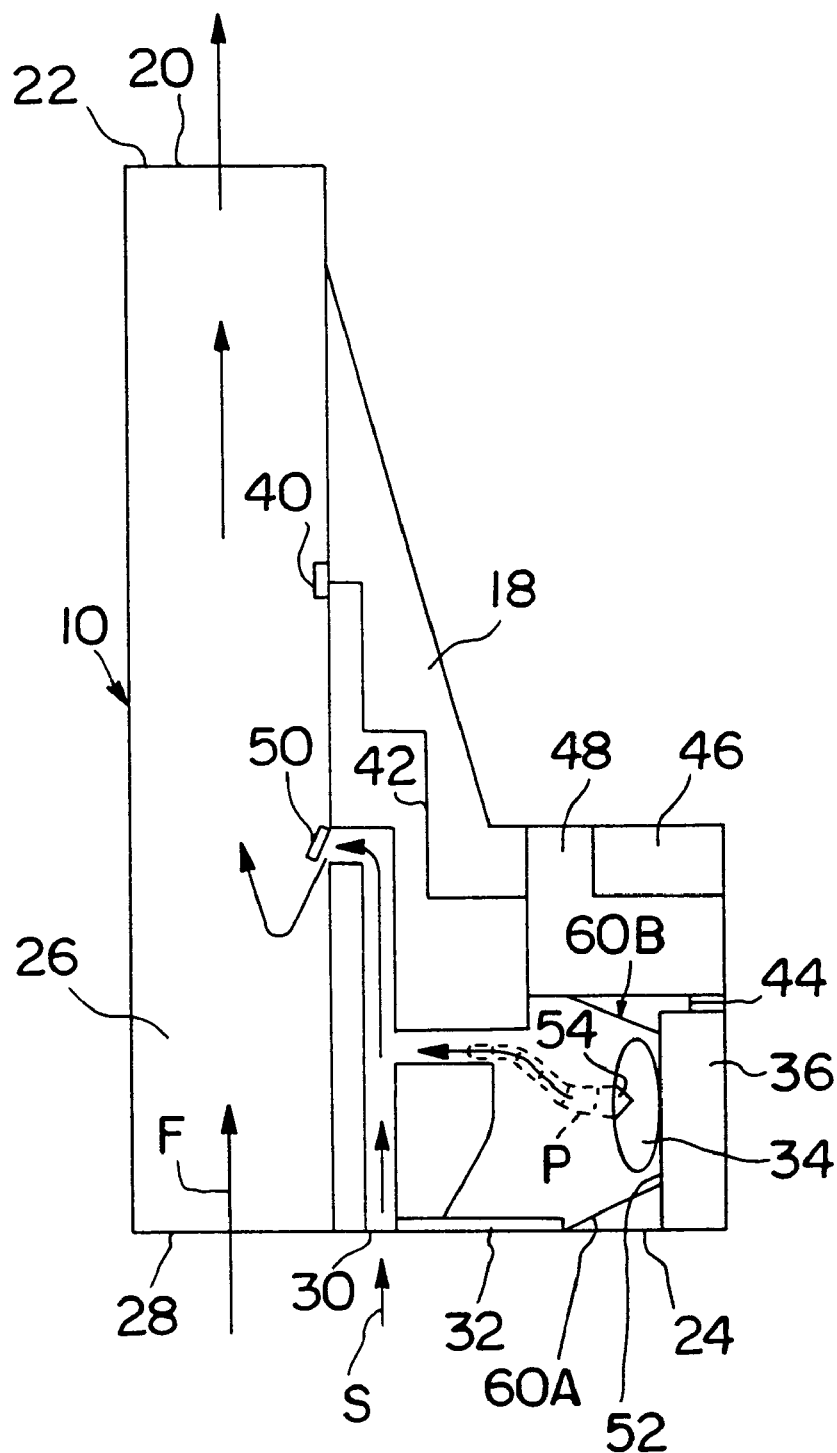
FIG. 3 is a longitudinal cross-sectional schematic view of the preferred embodiment of FIG. 1.

Referring to FIGS. 1–4, one preferred embodiment 10 of the inhaler of the present invention will now be made. Inhaler 10 includes a hard plastic or metal housing 18 having a generally L-shaped longitudinal cross-section. Housing 18 includes four air flow openings 20, 28, 30, and 32 (whose function in this embodiment of inhaler 10 of the present invention will be described more fully below). Inhaler 10 includes a main air flow passage 26 which extends the length of the housing 18 from the front 22 (at opening 20) to the rear 24 thereof (at opening 28) and has a generally square-shaped transverse cross-section, so as to permit air flow therethrough (denoted by arrow F in FIG. 1).

Secondary air conduit 31 is generally L-shaped and runs longitudinally from opening 30 in the rear 24 surface of the housing 18 to main passage 26. One-way flow valve 50 is mounted to the inner surface 33 of the main passage 26 via a conventional spring-biased hinge mechanism (not shown), which is adapted to cause the valve 50 to completely block air flow S through the conduit 31 to the main passage 26 when the pressure of the air flow F in the main passage 26 is below a predetermined threshold indicative of inhalation through the passage 26 by a user.

Powder dispensing chamber 51 is formed in housing 18 for holding a capsule 34 of powder medication to be inhaled. Housing 18 includes a moveable panel portion 32 in the rear 24 for permitting the capsule 34 to be introduced into the chamber 51 and placed on the seating 52 of vibration means 36 between guiding means 60A, 60B. Preferably, means 36 comprises a hard plastic or metallic protective shell 37 enclosing a piezoelectric vibrator 90. Preferably, vibrator 90 is mechanically coupled through the shell 37 via a disk (not shown) to the drug cartridge 34 so as to permit maximum vibratory energy to be transmitted from the vibrator 90 through the shell 37 to the cartridge 34. Guiding means 60A, 60B includes two surfaces which slant downwardly toward the seating 52 so as to permit easy introduction and retention of the capsule on the seating 52 in the chamber 51. Removable panel 32 includes another air inlet 34 for permitting additional air flow S2 from the chamber 51 through conduit 61 into conduit 31 during inhalation by the user. Preferably, panel 32 and housing 18 include conventional mating mounting means (not shown) for permitting the panel 32 to be removably resecurable to the housing by the user between introduction of fresh (i.e., completely full) capsules and removal of spent (i.e., empty) capsules.

Inhaler 10 also includes a conventional miniature air stream velocity or pressure sensor 40 mounted on the inner surface of the conduit 26 so as to sense the speed and/or pressure of the air stream F. Preferably, sensor 40 comprises a conventional spring-loaded flapper-yield switch which generates electronic signals indicative of the speed and/or pressure of the air stream F in the conduit 26, and transmits those signals via electrical connection 42 to electronic control circuitry 48 contained in housing 18 for controlling actuation of the vibrator means based upon those signals.

Preferably, the control circuitry 48 is embodied as an application specific integrated circuit chip and/or some other type of very highly integrated circuit chip. As will be described more fully below, the control circuitry 48 determines the amplitude and frequency of actuating power to be supplied from conventional power source 46 (e.g., one or more D.C. batteries) to the piezoelectric vibrator to thereby control vibration of the vibrator. The actuating power is supplied to the piezoelectric element 90 via electrical connection 44 between the vibrator and the circuitry 48.

Piezoelectric element 90 is made of a material that has a high-frequency, and preferably, ultrasonic resonant vibratory frequency (e.g., about 15 to 50 kHz), and is caused to vibrate with a particular frequency and amplitude depending upon the frequency and/or amplitude of excitation electricity applied to the piezoelectric element 90. Examples of materials that can be used to comprise the piezoelectric element 90 include quartz and polycrystalline ceramic materials (e.g., barium titanate and lead zirconate titanate). Advantageously, by vibrating the piezoelectric element 90 at ultrasonic frequencies, the noise associated with vibrating the piezoelectric element 90 at lower (i.e., non-ultrasonic) frequencies can be avoided.

Figure 4:
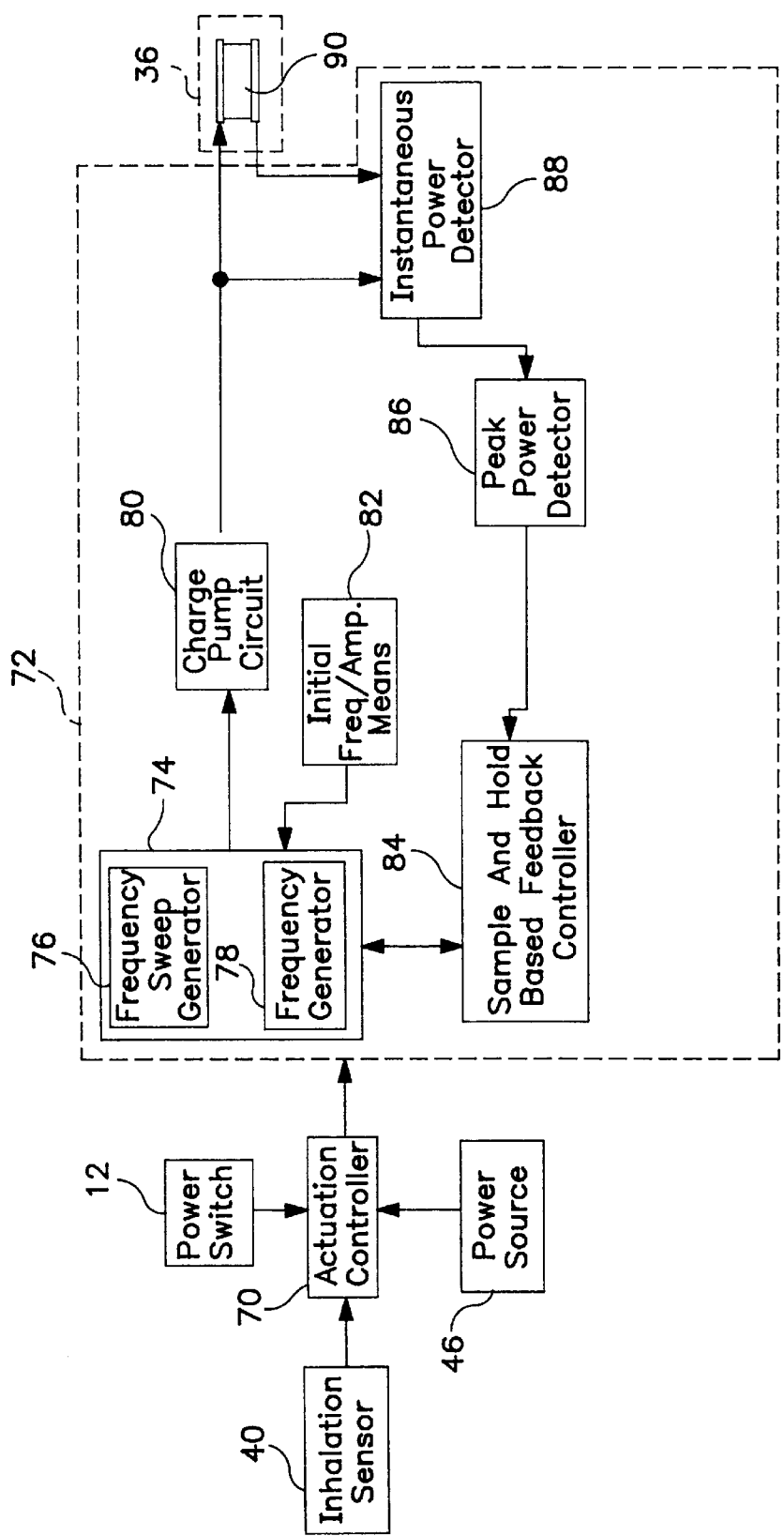
FIG. 4 is a functional block diagram of the vibration control system of the embodiment of FIG. 1.
Figure 5:
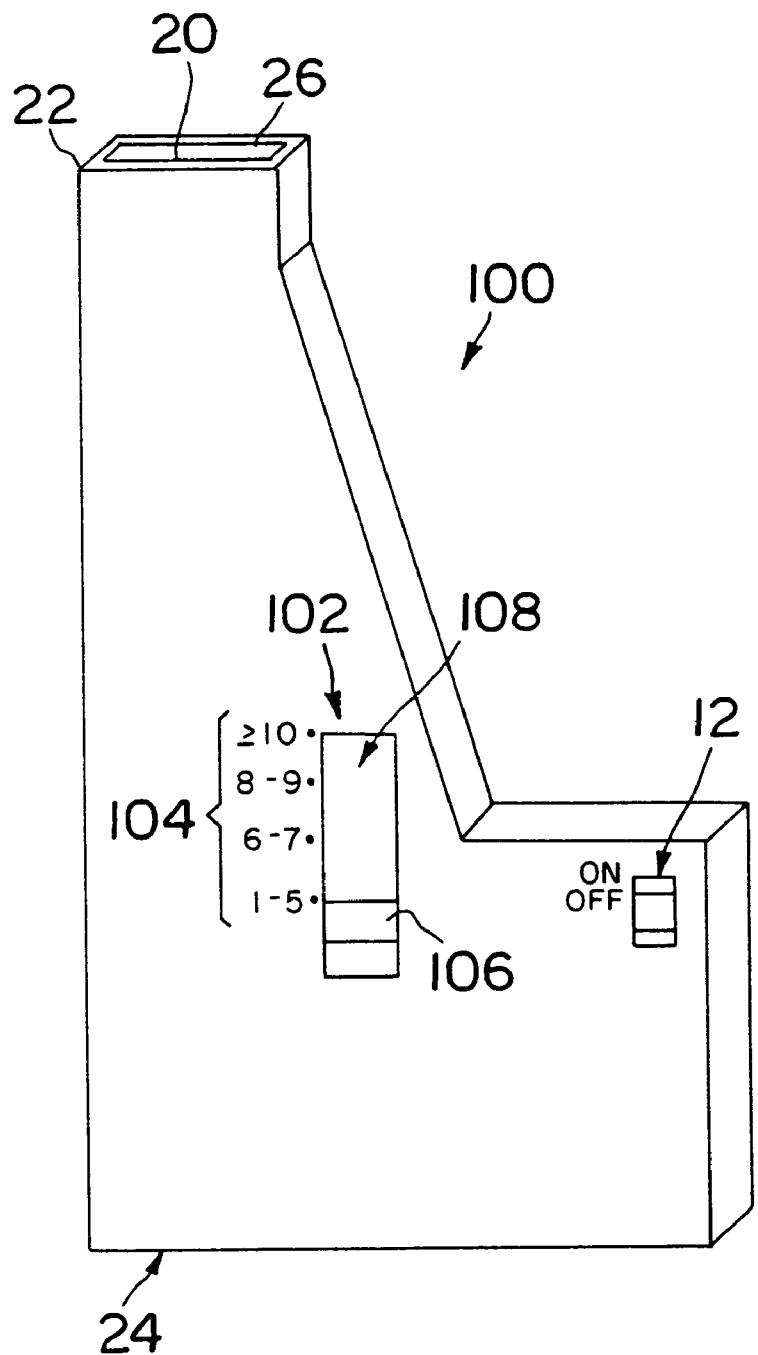
FIG. 5 is a perspective view of a second preferred embodiment of the inhaler of the present invention.
Figure 6:
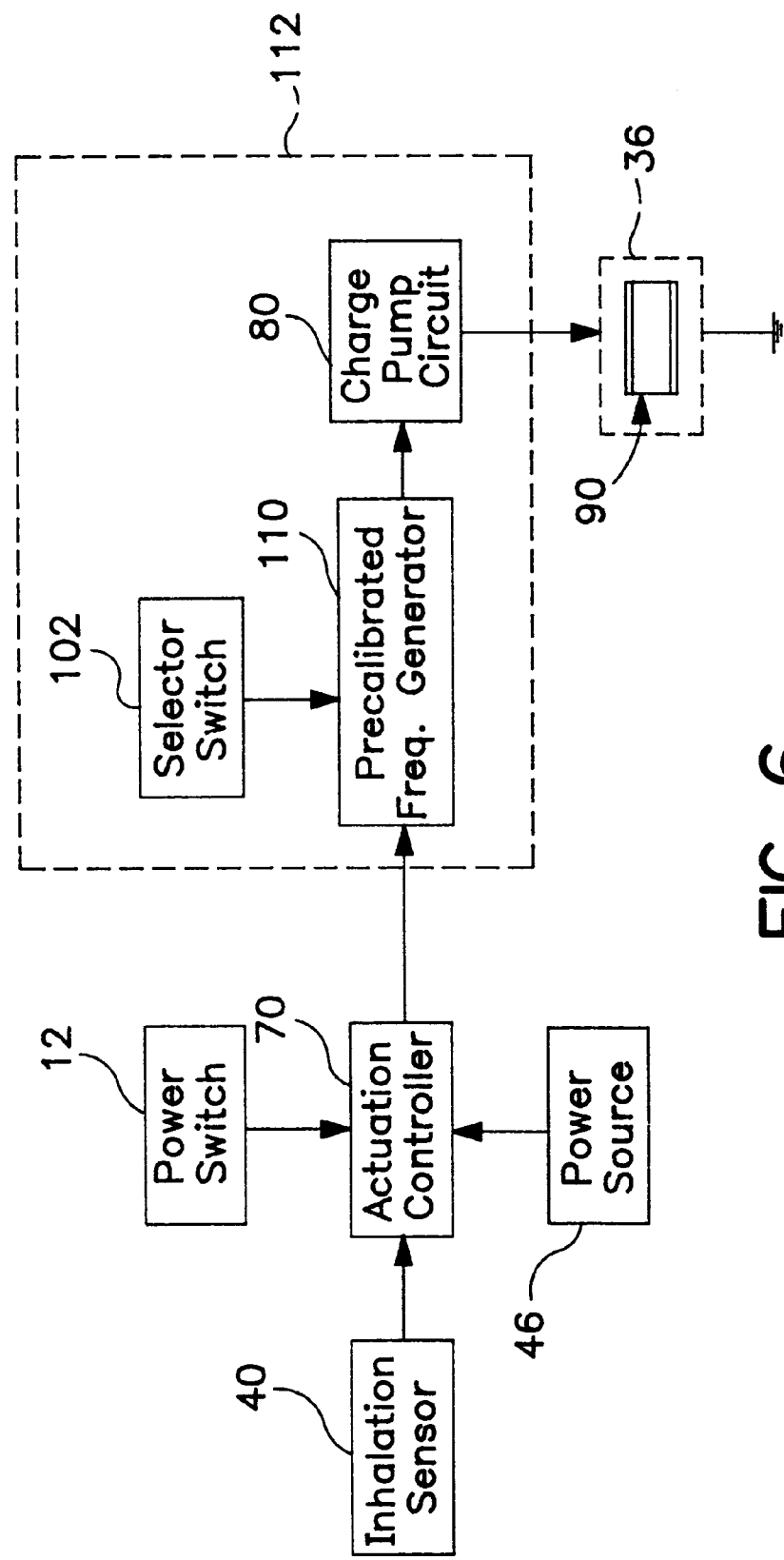
FIG. 6 is a functional block diagram of the vibration control system of the embodiment of FIG. 5.
Figure 7A:
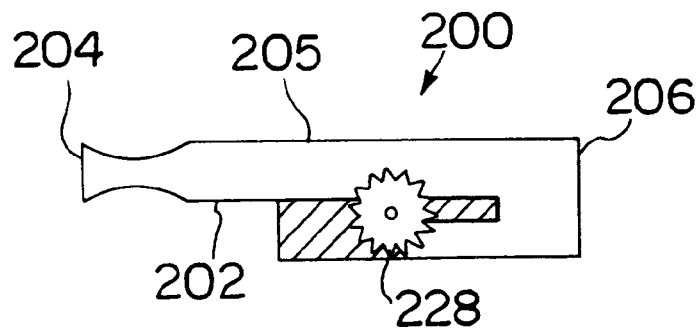
FIGS. 7A and 7B are side elevational views of yet another embodiment of the inhaler of the present invention.
Figure 7B:
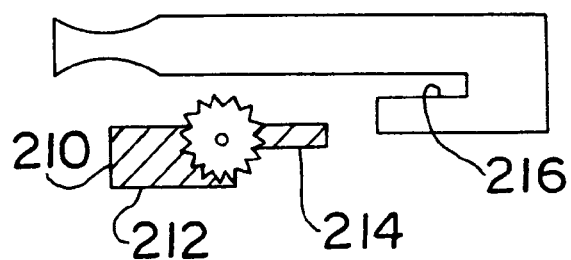
Figure 8:
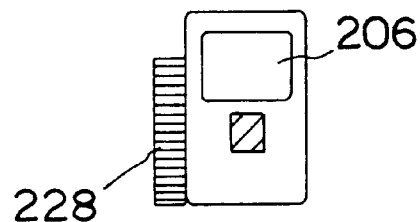
FIG. 8 is an end view of the embodiment of FIG. 7.
Figure 9:
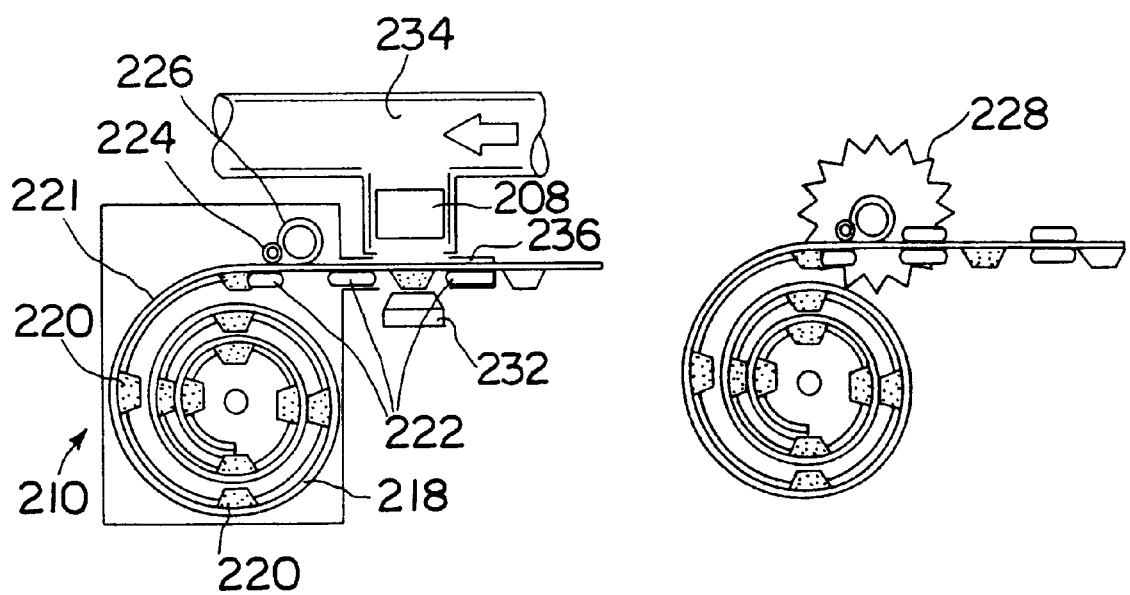
FIG. 9 is an enlarged cross-sectional view of the embodiment of FIG. 7.

Turning to FIG. 4, the various functional components and operation of the control circuitry 48 will now be described. As will be understood by those skilled in the art, although the functional components shown in FIG. 4 are directed to an analog realization of the control circuitry 48, the components of FIG. 4 could be appropriately modified to realize control circuitry 48 in a digital embodiment without departing from this embodiment 10 of the present invention.

Control circuitry 48 preferably includes actuation controller 70 and vibratory feedback control system 72. Acutation controller 70 comprises a conventional switching mechanism for permitting actuating power to be supplied from the power source 46 to the control system 72 depending upon the signals supplied to it from sensor 40 and the state of the power switch 12. In other words, controller 70 permits actuating power to be supplied from the source 46 to the system 72 when the sliding indicator bar 14 of switch 12 is set to the "ON" position in channel track 16 and the inhalation sensor 40 supplies signals to the controller 70 that indicate that the inhalation is occuring through the main passage 26. However, controller 70 does not permit actuating power to flow from the source to the system 72 when either the switch 12 is set to "OFF" or the signals supplied to the controller 70 from the sensor 40 indicate that inhalation is not taking place through the conduit 26.

When controller 70 first permits actuating power to be supplied from the source 46 to the feedback control system 72, the system 72 enters an initialization state wherein controllable means for supplying a predetermined frequency and amplitude of actuating electricity 74 is caused to generate control signals for causing conventional pump circuit 80 to generate an initial desired frequency and amplitude of actuating electricity based upon stored values thereof stored in the initialization memory means 82. Preferably, means 74 comprises conventional frequency sweep generator and frequency generator means 76 and 78, respectively. The signals generated by means 74 are then supplied to charge pump circuit 80 to cause circuit 80 to supply the piezoelectric element 90 with actuating electricity specified by the signals.

Preferably, the initial frequency and amplitude of actuating electricity supplied to the piezoelectric element 90 is pre-calibrated to cause the piezoelectric element 90 to vibrate at its resonance frequency when no powder cartridge or powder is placed on the means 36. As will be appreciated by those skilled in the art, maximum transfer of vibratory power from the piezoelectric element to the powder in the container 34 takes place when the piezoelectric element vibrates at its resonant frequency. It has been found that this results in maximum de-aggregation and suspension of the powder from the container 34 into the air to be inhaled by the user. However, when the container 36 or powder is placed on the vibrator means 36, the weight and volume of the powder container, and the weight, volume, and particular size of the powder to be suspended by the piezoelectric element can change the vibration characteristics of the piezoelectric element, and cause the piezoelectric element to vibrate at other than its resonant frequency. This can result in reduced vibratory energy transfer to the powder from the piezoelectric element, and thereby, lessen the efficiency of the piezoelectric element in de-aggregating and suspending the powder in the air inhaled by the user.

The feedback control system 72 of the present invention overcomes this problem. In control system 72, after the initial frequency and amplitude of actuating electricity are supplied to the piezoelectric element 90, the frequency generating means 74 systematically generates control signals indicative of many different amplitudes and frequencies of electricity for being supplied to the piezoelectric element 90 by the circuit 80. As the generating means 74 "cycles through" the different frequencies and amplitudes, the instantanous power transfer characteristics of the piezoelectric element 90 for each of these different frequencies and amplitudes are determined by the detector 88, which transmits this information to the peak power detector 86. Peak detector 86 analyzes the instantaneous power transfer characteristics of the piezoelectric element 90 and signals the sample and hold feedback controller 84 when the power transfer characteristics are at local maxima. The controller 84 correlates these local maxima with the frequencies and amplitudes commanded by the generator 74 to be supplied to the piezoelectric element 90.

After the frequency generator 74 has finished its sweep through the frequencies and amplitudes of power supplied to the piezoelectric element 90, the controller 84 causes the generator 74 to cycle through the frequencies and amplitudes of power that resulted in local maxima, and then determines which of these frequencies and amplitudes results in optimal power transfer characteristics through the piezoelectric element 90.

In operation of embodiment 10, the drug-containing package 34 is punctured and inserted onto the surface 52 of vibrator 36 in chamber 51 in the manner described previously. The power switch is placed in the "ON" position and the user inhales air through the conduit 26, air flow F is generated through conduit 26. This causes one-way valve 50 to deflect to admit air flow S through opening 30 into conduit 26, and also causes air flow S2 through opening 34 and chamber 51 into conduit 26. The inhalation of air stream F is sensed by sensor 40 and is signaled to actuation controller 70, which causes power to be supplied to the controller 72. The controller 72 then adjusts the amplitude and frequency of actuating power supplied to the piezoelectric element until they are optimized for the best possible de-aggregation and suspension of the powder P from the capsule into the air stream F via air flows S and S2.

Turning to FIGS. 5–6, a second preferred embodiment 100 of the present invention will now be described. It should be appreciated that unless specifically indicated to the contrary, the components and operation of embodiment 100 are substantially identical to those of embodiment 10. In embodiment 10, the feedback controller 72 of embodiment 10 is replaced with a pre-calibrated controller 112. Controller 112 includes precalibrated frequency/amplitude control signal generator 110 which supplies control signals to pump circuit 80 based upon signals supplied to it from user-actuable frequency/amplitude controller switch 102. Switch 102 includes indicator means 106 slidably mounted in channel track 108 and permits a user to command the generator 110 to generate control signals for causing the pump 80 to supply amplitude and frequencies of actuating power to the piezoelectric element for optimally suspending powders of differing, pre-calibrated particular sizes. For example, when the selector switch is set to the "1–5" position, the generator 110 may be pre-programmed to generate control signals for causing the pump 80 to supply to the piezoelectric element 90 actuating electricity having a frequency and amplitude for optimally suspending powder particles between about 1 and 5 microns in size. Of course, it will appreciated that the pre-calibrated optimal frequency and amplitude values programmed in generator 110 are based upon an expected weight and volume the container 34 and powder contained therein. Thus, in order for the inhaler 100 to be able to optimally suspend the powder, the weight and volume of the container 34 and powder contained therein cannot different significantly from the expected values thereof upon which the pre-calibration values programmed into the generator 110 were based.

Referring now to FIGS. 7 to 9, there is shown yet another embodiment 200 of the inhaler made in accordance with the present invention. The inhaler 200 comprises a generally U-shaped, hollow housing 202 having a mouthpiece 204 at one end of one leg 205 thereof, and an air inlet opening 206 at the opposite end of the same leg 205. Referring in particular to FIG. 9, a passageway 208 is formed in leg 205 intermediate of mouthpiece 204 and inlet 206, and communicates with a disposable drug cartridge indicated generally at 210 as will be described in detail hereinafter.

Disposable drug cartridge 210 comprises an outer housing 212 which includes a tab 214 for slidably mounting in a recess 216 formed integrally with housing 202. Drug cartridge 210 includes a coiled tape 218 carrying a plurality of spaced bubbles or wells 220 for carrying a dry powder medicament. A release film 221 covers and seals wells 220. Tape 218 is formed as a coil, and threaded between a first guide platen 222 and pinch roller 224. Pinch roller 224 in turn is driven by a take-up spool 226 which in turn is driven by a thumbwheel 228 which is mounted on a common shaft with the take-up spool 226. In use, release film 221 is peeled from the tape 218, whereby to expose wells 220, one at a time, as the film is advanced through the cartridge, and the release film 221 is collected on take-up spool 226.

Completing cartridge 210 is a piezoelectric element 232 for mechanically engaging wells 220, one at a time, as they are selectively advanced in position over and in contact with the piezoelectric element 232. Tape 218 also preferably includes detent means or the like for indexing the tape so that a selected well 220 is automatically positioned over piezoelectric element 232. Finally, an actuating circuit and power supply, similar to that previously discussed, is mounted within cartridge 210.

Preferably, but not necessarily, the interior walls of housing 202 are coated with a metallized coating 234 so as to obviate possible electrostatic charge buildup within the housing.

Also, if desired, as shown in phantom in FIG. 9, an auxiliary air inlet 236 may be provided immediately upstream of the piezoelectric element 232 for assisting in carrying powder particles as they are energized by the piezoelectric element.

Various changes may be made in the invention. For example, the actuating circuit, and/or the power supply and/or the piezoelectric element may be carried by the housing 202, as opposed to the cartridge 210. Also, electrostatic potential means 238 may be included for driving the vibrated powder into the gas stream. If desired, the electrostatic potential may be controlled to separate the different size particles in the powder.

It will be appreciated that although the foregoing detailed description proceeded with reference being made to preferred embodiments and methods of use, the present invention is not intended to be limited to these preferred embodiments and methods of use. Rather, the present invention is of broad scope and is intended to be limited only as set forth in the accompanying claims.

What is claimed is:

1. A dry powder inhaler comprising, a first chamber in which means for deaggregating a dry powder by vibrating said powder, a first air flow passageway in which the deaggregated powder can be separated by size, and a second air flow passageway in which the size-separated deaggregated powder can be picked up and carried for inhalation by a patient.

2. An inhaler according to claim 1, and further comprising at least one detector for detecting velocity of said air flow in said second air flow passageway.

3. An inhaler according to claim 2, and further comprising a controller adapted to automatically actuate or deactivate said vibrator in response to signals from the detector.

4. An inhaler according to claim 3, wherein said detector is adapted to actuate said vibrator based on a minimum threshhold which is indicative of inhalation of gas from said inhaler.

5. An inhaler according to claim 1, and further comprising at least one detector for detecting air pressure in said second air flow passageway.

6. An inhaler according to claim 1, wherein said vibrator comprises a piezoelectric vibrator.

7. An inhaler according to claim 1, and further comprising, a dispenser for dispensing said powder based upon control signals supplied to said dispenser by a controller, said control signals being generated by said controller based upon, at least in part, on at least one detected characteristic of said gas stream.

8. An inhaler according to claim 7, wherein said dispenser causes powder dispensed therefrom to directly contact a surface of said vibrator.

9. An inhaler according to claim 1, and further comprising, a plurality of gas inlets, and at least one one-way valve in at least one of said plurality of inlets, said valve being adapted to permit flow of gas into said inhaler therethrough upon inhalation of gas from said inhaler.

10. An inhaler according to claim 1, wherein at least a portion of the inner surface of the housing of the inhaler is metallized.

11. An inhaler according to claim 1, and further including a removable cartridge for containing said powder.

12. An inhaler according to claim 11, wherein powder is contained within said cartridge as discrete aliquots sequentially disposed on an elongate tape.

13. An inhaler according to claim 12, wherein said aliquots are predetermined dosage size aliquots.

14. An inhaler according to claim 12, wherein said tape comprises wells for carrying the powder.

15. An inhaler according to claim 14, wherein said well as are covered by a release film.

16. An inhaler according to claim 15, and further comprising means for collecting said release film within said cartridge.

17. An inhaler according to claim 12, wherein said removable cartridge also comprises a piezoelectric vibrator.

18. An inhaler according to claim 17, and further comprising means for advancing said tape sequentially past said piezoelectric vibrator.

19. A dry powder inhaler comprising, a first chamber containing a piezoelectric vibrator for vibrating a powder, and a controller for controlling supply of actuating electricity to said vibrator so as to cause vibration of said powder whereby to suspend at least a portion of said powder into air, a first air flow passageway in which the suspended powder may be separated by size, and a second air flow passageway in which the size-separated powder can be picked up and carried for inhalation by a patient.

20. An inhaler according to claim 19, wherein said portion has an average particulate size between 0.5 and 10 microns.

21. An inhaler according to claim 20, wherein said portion has an average particulate size between 1 and 5 microns.

22. An inhaler according to claim 19, wherein at least a portion of the inner surface of the housing of the inhaler is metallized.

23. An inhaler according to claim 19, wherein frequency of said vibration is at least about 12 KHz.

24. An inhaler according to claim 19, wherein said controller includes a user-actuable control for permitting a user to control actuation of said vibrator based upon a selected type of powder.

25. An inhaler according to claim 19, wherein said controller also is adapted to control frequency and amplitude of actuating electricity.

26. A dry powder inhaler comprising, a first chamber containing an electrically driven vibrator for vibrating a powder whereby to deaggregate said powder, a controller for controlling supply of actuating electricity to said vibrator based, at least in part, upon detected power transfer characteristics of said vibrator, a first air flow passageway in which the vibrated powder can be separated by size, and a second air flow passageway in which the size-separated powder can be carried for inhalation by a patient.

27. An inhaler according to claim 26, wherein said detected power transfer characteristics include whether maximum power is being transferred to said vibrator.

28. An inhaler according to claim 26, wherein said controller is adapted to control amplitude and frequency of said electricity based upon said detected characteristics.

29. An inhaler according to claim 26, wherein said controller is adapted to control the supply of power so as to ensure that maximum power is transferred to said vibrator.

* * * * *

UNITED STATES PATENT AND TRADEMARK OFFICE
CERTIFICATE OF CORRECTION

PATENT NO. : 6,026,809　　　　　　　　　　　　　　　　　　　　　Page 1 of 1
DATED : February 22, 2000
INVENTOR(S) : Abrams et al.

It is certified that error appears in the above-identified patent and that said Letters Patent is hereby corrected as shown below:

<u>Column 9,</u>
Lines 21-22, change "in which" to -- having --.

Signed and Sealed this

Twelfth Day of February, 2002

*Attest:*

*Attesting Officer*　　　　　　　　JAMES E. ROGAN
　　　　　　　　　　　　　　*Director of the United States Patent and Trademark Office*